US010670006B2

(12) United States Patent
Blenkush

(10) Patent No.: US 10,670,006 B2
(45) Date of Patent: Jun. 2, 2020

(54) HOSE BRACKET FOR TEXTURE SPRAYER

(71) Applicant: Graco Minnesota Inc., Minneapolis, MN (US)

(72) Inventor: William M. Blenkush, Becker, MN (US)

(73) Assignee: Graco Minnesota Inc., Minneapolis, MN (US)

( * ) Notice: Subject to any disclaimer, the term of this patent is extended or adjusted under 35 U.S.C. 154(b) by 373 days.

(21) Appl. No.: 15/411,013

(22) Filed: Jan. 20, 2017

(65) Prior Publication Data

US 2017/0211568 A1 Jul. 27, 2017

Related U.S. Application Data

(60) Provisional application No. 62/286,005, filed on Jan. 22, 2016.

(51) Int. Cl.

| | |
|---|---|
| ***F04B 43/12*** | (2006.01) |
| ***B05B 7/24*** | (2006.01) |
| ***F04B 43/00*** | (2006.01) |
| ***B05B 7/04*** | (2006.01) |
| ***F04B 17/03*** | (2006.01) |

(Continued)

(52) U.S. Cl.

CPC ........ *F04B 43/1253* (2013.01); *B05B 7/0416* (2013.01); *B05B 7/2489* (2013.01); *F04B 17/03* (2013.01); *F04B 17/06* (2013.01); *F04B 43/0072* (2013.01); *F04B 43/1261* (2013.01); *B05B 7/0093* (2013.01); *B05B 9/042* (2013.01)

(58) Field of Classification Search

CPC .......... B05B 9/042; F04B 17/06; F04B 17/03; F04B 2205/09; F04B 43/0072; F04B 43/1215; F04B 43/1253

USPC ........ 417/477.1, 477.3, 477.6, 477.8, 477.13

See application file for complete search history.

(56) References Cited

U.S. PATENT DOCUMENTS 2,696,173 A 12/1954 Jensen
3,402,673 A 9/1968 Ballentine et al.

(Continued)

FOREIGN PATENT DOCUMENTS

| | | | |
|---|---|---|---|
| CN | 1658977 | A | 8/2005 |
| CN | 101532485 | A | 9/2009 |
| EP | 2397695 | A1 | 12/2011 |

OTHER PUBLICATIONS

English Translation of Chinese Office Action dated Mar. 6, 2020 and cited on IDS submitted on Mar. 06, 2020 (Year: 2020).*

(Continued)

*Primary Examiner* — Dominick L Plakkoottam

(74) *Attorney, Agent, or Firm* — Kinney & Lange, P.A.

(57) ABSTRACT

A peristaltic pump comprises a drive assembly, a hose pump, and a hose bracket. The drive assembly is rotatably disposed within a frame to move a roller along a pumping path with respect to the frame. The pump hose has rigid hose ends connected by a bendable hose section with limited flexibility tending to bias the pump hose towards a substantially unbent shape. The hose bracket has a rigid body with a first central opening sized to receive the rigid hose ends at first and second retention locations, such that the natural bias of the pump hose towards a substantially unbent shape retains the hose ends within the first and second retention locations, positioning the bendable hose section along the pumping path of the roller.

20 Claims, 4 Drawing Sheets

(51) Int. Cl.

| | |
|---|---|
| ***F04B 17/06*** | (2006.01) |
| *B05B 7/00* | (2006.01) |
| *B05B 9/04* | (2006.01) |

(56) References Cited

U.S. PATENT DOCUMENTS 3,674,383 A 7/1972 Iles
4,240,583 A 12/1980 Hughes
4,387,872 A * 6/1983 Hogue .................. A47B 57/42 248/220.43
4,515,535 A * 5/1985 D'Silva ............... F04B 43/1253 403/DIG. 1
4,552,516 A 11/1985 Stanley
4,585,399 A * 4/1986 Baier .................. F04B 43/1253 417/477.12
5,342,182 A 8/1994 Montoya et al.
5,433,588 A * 7/1995 Monk ................. F04B 43/1253 417/477.2
8,152,498 B2 4/2012 Bunoz
8,182,241 B2 5/2012 Fulmer
8,491,285 B2 7/2013 Haser et al.
8,597,247 B2 * 12/2013 Peterson ........... A61M 5/14232 604/151
9,004,886 B2 * 4/2015 Beck ................... F04B 43/0081 417/476
9,366,245 B2 * 6/2016 Ono .................... F04B 43/1253
2005/0254879 A1 * 11/2005 Gundersen ............ B05B 7/2489 401/48
2005/0254978 A1 * 11/2005 Huber ................. A47L 15/4418 417/477.1
2013/0177463 A1 * 7/2013 Cheng ................. F04B 43/1261 417/477.1
2014/0010675 A1 * 1/2014 Kent ..................... F04B 43/009 417/53
2015/0204321 A1 7/2015 Schnekenburger et al.

OTHER PUBLICATIONS

First Office Action from Chinese Patent Application No. 2017100477194, dated Oct. 25, 2018, 16 pages.

First Office Action from Chinese Patent Application No. 2017100477194, dated Jul. 9, 2019, 17 pages.

Third Office Action dated Mar. 6, 2020 received for corresponding Chinese Patent Application No. 2017100477194, 6 pages.

* cited by examiner

HOSE BRACKET FOR TEXTURE SPRAYER

CROSS-REFERENCE TO RELATED APPLICATION(S)

This application claims the benefit of U.S. Provisional Application No. 62/286,006 filed Jan. 22, 2016 for "Hose Bracket for Texture Sprayer" by William M. Blenkush, which is herein incorporated by reference.

BACKGROUND

The present invention relates generally to texture sprayers, and more particularly to a hose bracket for a pump hose of a texture sprayer using a peristaltic pump.

Texture sprayers are commonly used apply materials or mixtures of materials to walls, ceilings, or other surfaces. Such materials can for example include solvents, adhesives, oils, paints, and flowable solids, including materials with high viscosity or highly granular texture. Peristaltic pumps are used in some texture sprayers.

Peristaltic pumps (including for pressure sprayers) use pump hoses that are compressed by the movement of rollers using a drive assembly, thereby driving the contents of the pump hose in a pumping direction and creating line pressure. While in use, a pump hose must be secured along a pumping path of the rollers. Pump hoses see heavy wear, and must consequently be replaced frequently.

SUMMARY

In one aspect, the present invention is directed toward a peristaltic pump comprising a drive assembly, a hose pump, and a hose bracket. The drive assembly is rotatably disposed within a frame to move a roller along a pumping path with respect to the frame. The pump hose has rigid hose ends connected by a bendable hose section with limited flexibility tending to bias the pump hose towards a substantially unbent shape. The hose bracket has a rigid body with a first central opening sized to receive the rigid hose ends at first and second retention locations, such that the natural bias of the pump hose towards a substantially unbent shape retains the hose ends within the first and second retention locations, positioning the bendable hose section along the pumping path of the roller.

In another aspect, the present invention is directed to an installation method for a pump hose of a peristaltic pump. According to this method, a flexible section of the pump hose is bent to bring together hose couplings of the pump hose at either end of the flexible section. The hose couplings are inserted into a central opening of an outer hose bracket, then released such that a natural unbending bias of the flexible section retains the hose couplings at mounting locations of the first central opening. An inner hose bracket is attached to simultaneously abut the hose couplings and the outer hose bracket, thereby discouraging the pump hose from disengaging from the outer hose bracket. The inner and outer hose brackets are locked together into location where the pump hose abuts rollers of the peristaltic pump.

The present summary is provided only by way of example, and not limitation. Other aspects of the present disclosure will be appreciated in view of the entirety of the present disclosure, including the entire text, claims, and accompanying figures.

Figure 1:
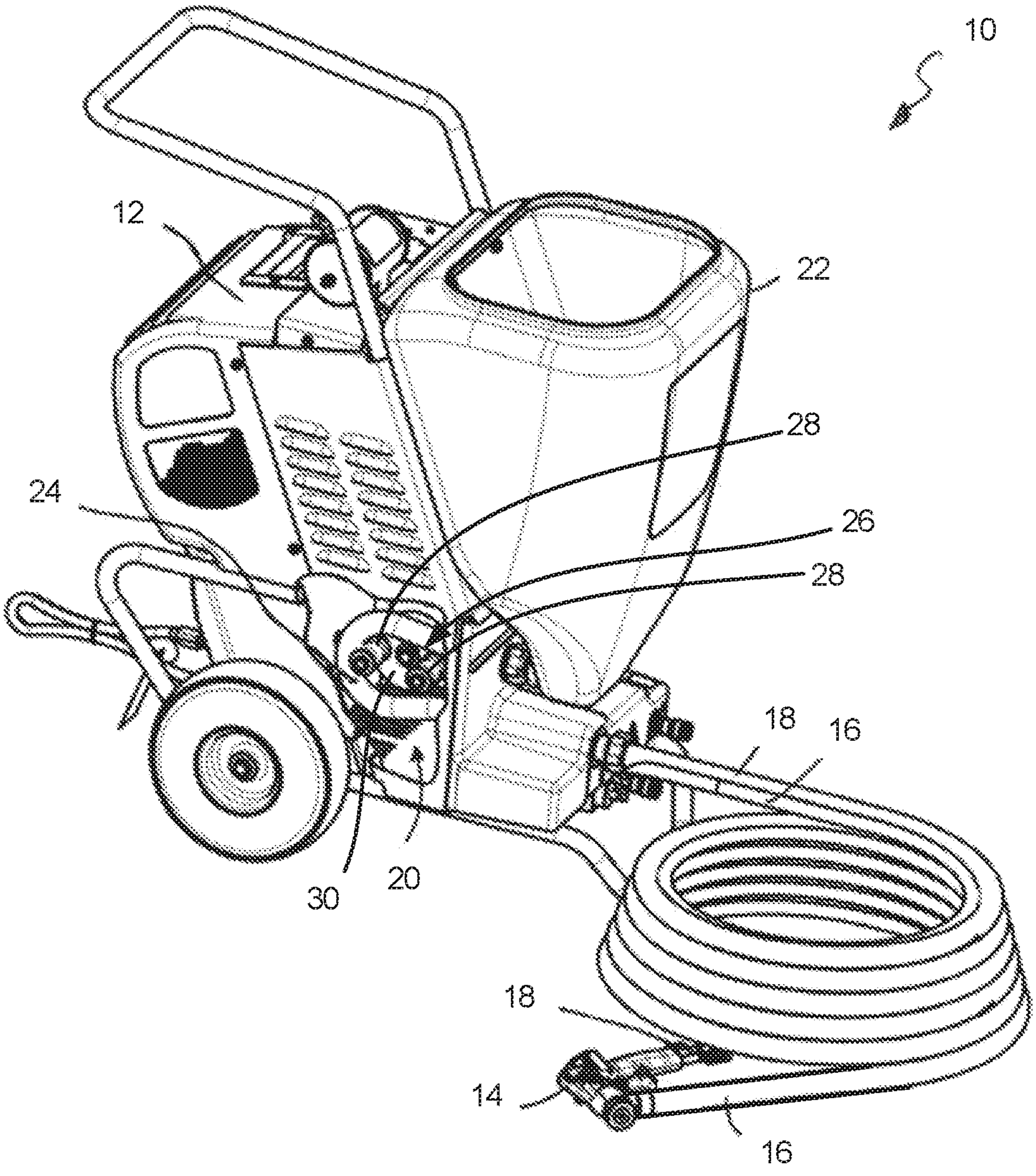
FIG. 1 is a perspective view of a texture sprayer system.

While the above-identified figures set forth one or more embodiments of the present disclosure, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features and components not specifically shown in the drawings.

DETAILED DESCRIPTION

The present invention provides a hose bracket that simplifies installation of a pump hose by utilizing the hose's natural stiffness, which biases the hose towards an open shape. The hose is installed within the bracket by bending hose couplings of the hose together, and inserting these rigid hose ends into a central opening of the bracket. The natural bias of the hose retains it against frame, which supplies an inward-facing retaining force opposed to the bias of the hose. By contrast, prior art pump hose brackets for peristaltic pumps have had no central opening, and have instead secured hose couplings of pump hose in open ends of a bracket plate. This open-ended design does not make use of the natural opening bias of the hose, and consequently requires that the hose be held in place on the bracket (either manually or with specialized equipment) while it is locked into place via additional hardware.

FIG. 1 is a perspective view of texture sprayer system 10, which includes main unit 12 and spray gun 14. Main unit 12 is a pneumatic texture sprayer connected to spray gun 14 by fluid hose 16 and air hose 18. Spray gun 14 is a handheld, manually triggered pneumatic applicator that receives fluid or flowable solid texture from fluid hose 16, and pressurized gas from air hose 18. Spray gun 14 includes a trigger which, when actuated, opens at least one valve within spray gun 14, thereby mixing pressurized gas from air hose 18 and texture from fluid hose 16 within spray gun 14. This mixture is expelled from a nozzle of spray gun 14, e.g. in a flat or conical spray pattern.

Main unit 12 of texture sprayer 10 contains an electrical system, controls, an electric motor (e.g. a brushless or universal-type motor), an air compressor (e.g. an oilless air compressor or analogous pressurizing system), peristaltic pump 20, and texture receptacle 22. Peristaltic pump 20 receives and pressurizes texture from texture receptacle 22, and supplies this pressurized material to spray gun 14 via fluid hose 16. Peristaltic pump 20 includes pump hose 24 and pump drive assembly 26 with rotor 28 on rollers 30. Pump hose 24 is a short, replacable hose segment within peristaltic pump, fluidly between texture receptacle 22 and fluid hose 16. During operation of peristaltic pump 20, pump drive assembly 26 engages pump hose 24 such that rotation of rotor 28 (driven by the electric motor; not shown) causes rollers 30 to roll along pump hose 24 and compress pump hose 24, peristaltically driving fluid in a flow direction through peristaltic pump 20, towards spray gun 14. In some embodiments of the present invention pump drive assembly 26 may be retractable from pump hose 24 while not actively pumping, so as to prevent clogging, and may only engage or compress pump hose 24 while actively pumping. Pump hose 24 experiences significant wear during operation of peristaltic pump 20, particularly when pumping coarse materials such as flowable solids. Pump hose 24 can accordingly be removed and replaced easily and quickly by means of the current invention, as explained below.

Figure 2:
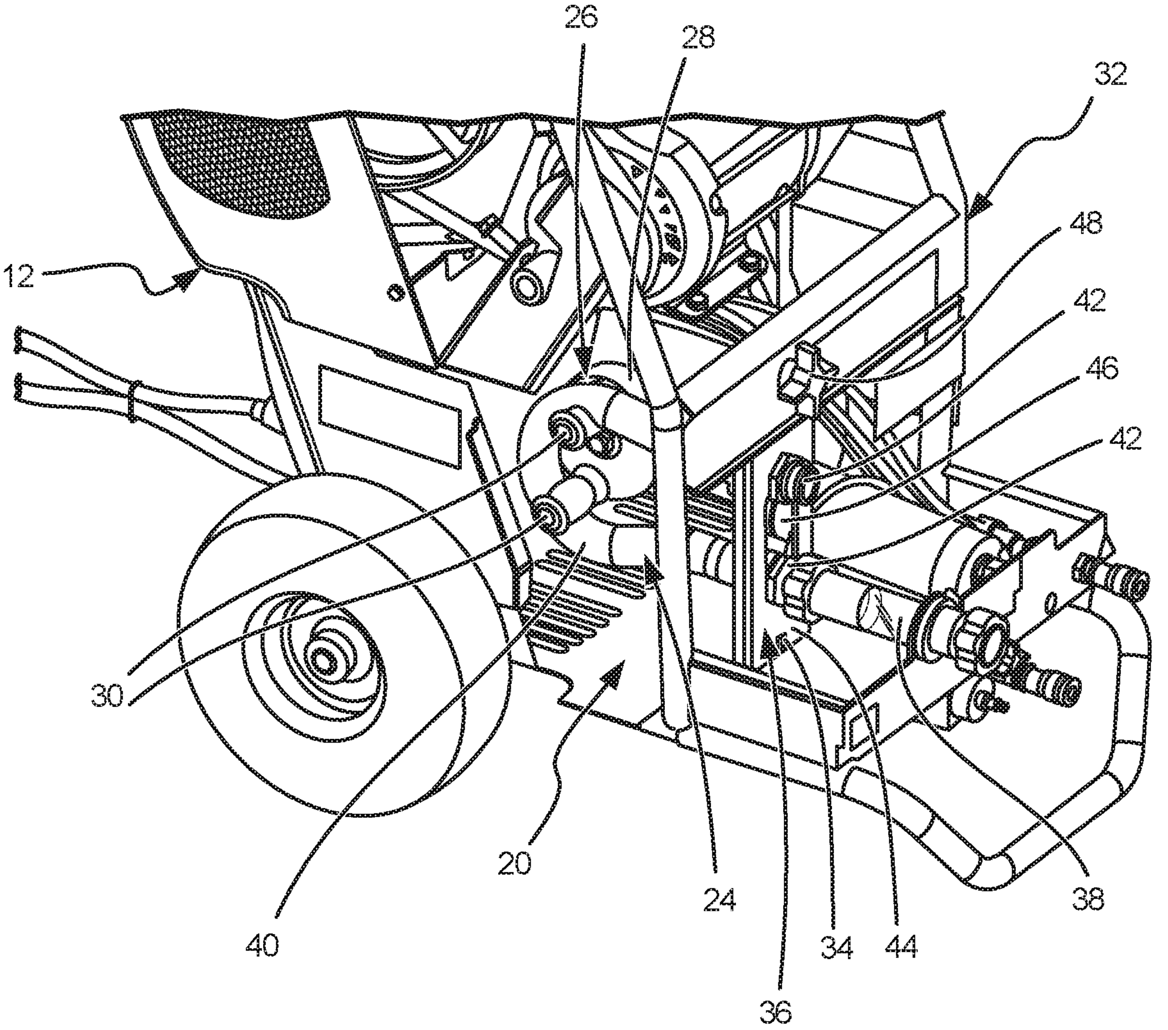
FIG. 2 is a perspective view of an exposed pump section of the texture sprayer of FIG. 1, illustrating a pump hose in a hose bracket assembly.

FIG. 2 is a perspective view of an exposed section of main unit 12 surrounding peristaltic pump 20. FIG. 2 illustrates pump hose 24, pump drive assembly 26 (with rollers 30 and rotor 28), frame 32 (with slot 34), hose bracket assembly 36, and extension pipe 38. Pump 24 further includes flexible section 40 extending between hose couplings 42. FIG. 2 additionally illustrates outer bracket 44 and inner bracket 46 of hose bracket assembly 36, and bracket fastener 48.

Frame 32 is a rigid support structure that makes up a body of main unit 12. Hose bracket assembly 36 is a removable two-piece locking structure made up of outer bracket 44 and inner bracket 46, which together retain pump hose 24 in position for engagement with rollers 30 of pump drive assembly 26. Outer and inner brackets 44 and 46 are rigid structural elements that can, for example, be plates formed of metal such as steel. Hose bracket assembly 36 secures pump hose 24 at hose couplings 42, and locks into place on frame 32, thereby positioning flexible section 40 in a substantially U-shaped or horseshoe-shaped orientation within peristaltic pump 20, adjacent rollers 30. Outer bracket 44 and inner bracket 46 are described in greater detail hereinafter. Both outer bracket 44 and inner bracket 46 fit into slot 34, a groove or slit in the base of frame 32. Hose bracket assembly 36 is locked into place on frame 32 by bracket fastener 48, which can for example be a screw or bolt disposed through frame 32, outer bracket 44, and inner bracket 46. Once pump hose 24 is installed on bracket assembly 36 (see FIGS. 5A-5C, discussed below), bracket assembly 36 is installed on frame 32 by first inserting a bottom end of hose bracket assembly 36 into slot 34, then securing the opposite end of hose bracket assembly 36 via bracket fastener 48. Bracket fastener 48 prevents hose bracket assembly 36 from escaping slot 34.

Hose bracket assembly 36 engages hose couplings 42 of pump hose 24. Hose couplings 42 can, for example, be rigid metal hose ends formed of metal such as steel or aluminum. In the depicted embodiment, each hose coupling 42 has two hexagonal flanges separated by a neck or gap (see FIG. 6, discussed below) that receives hose bracket assembly 36. In alternative embodiments hose couplings 42 can have other shapes (e.g. circular). Although hose couplings 42 are identical in the illustrated embodiment, alternative pump hoses 24 may have hose couplings that are not identical.

Hose couplings 42 include fastening features to engage downstream and upstream fluid handling elements. In the illustrated embodiment hose couplings 42 are threaded to mate in a fluid seal with fluid receptacle 22 and extension pipe 38. Extension pipe 38 is a short section of pipe or hose extending pump hose 24 to a hookup location for fluid hose 16 (see FIG. 1). In some embodiments, however, pump hose 24 may connect directly to fluid hose 16.

Hose bracket assembly 36 retains and positions pump hose 24 for compression by rollers 30 of peristaltic pump 20. Because hose bracket assembly 36 is easily removable and pump hose 24 can be quickly installed in or removed from hose bracket assembly 36 without need for specialized equipment, hose bracket assembly 36 facilitates replacement of pump hose 24. As mentioned above, pump hose 24 is a disposable component that may require frequent replacement for some applications.

Figure 4:
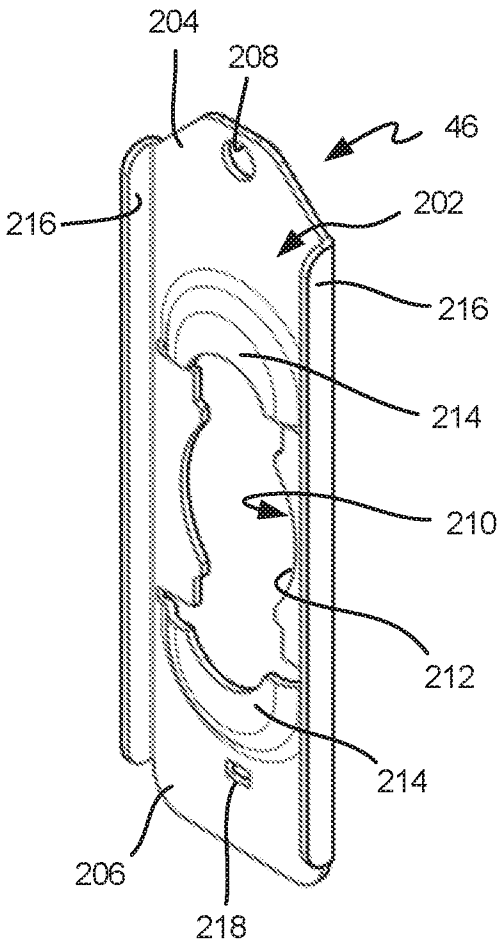
FIG. 4 is a perspective view of an inner bracket of the hose bracket assembly of FIG. 2.
Figure 3:
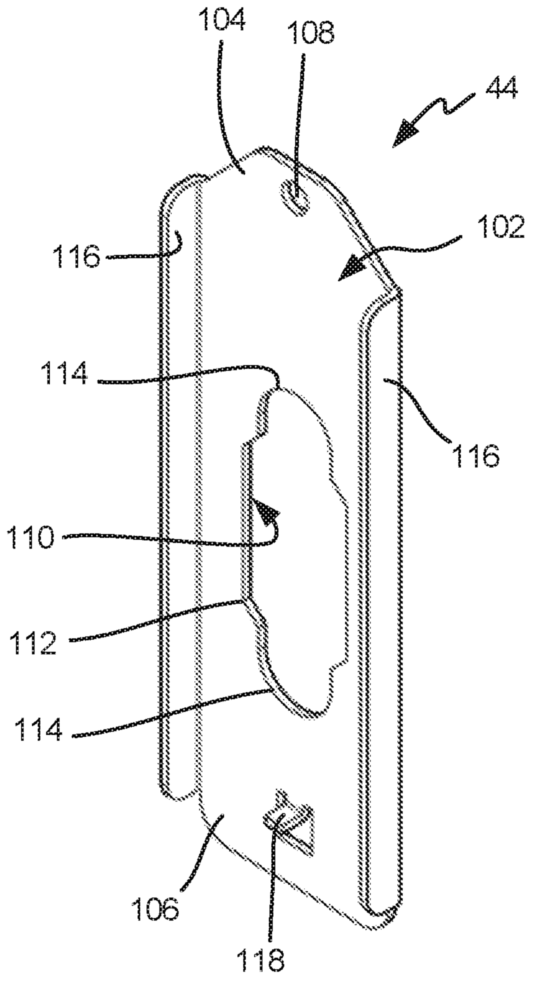
FIG. 3 is a perspective view of an outer bracket of the hose bracket assembly of FIG. 2.

FIGS. 3 and 4 are perspective views of outer bracket 44 and inner bracket 46, respectively. Outer bracket 44 includes outer plate 102 (with top and bottom outer plate ends 104 and 106, respectively), outer fastener hole 108, outer central opening 110 (with outer opening perimeter 112 defining mountings 114), outer stiffening flanges 116, and tab 118. Inner bracket 46 similarly includes inner plate 202 (with top and bottom inner plate ends 204 and 206, respectively), inner fastener hole 208, inner central opening 210 (with inner opening perimeter 212), retainers 214, inner stiffening flanges 216, and slot 218. Outer bracket 44 and inner bracket 46 mate together to form hose bracket assembly 26, as described above with respect to FIG. 3.

In the illustrated embodiments, outer bracket 44 and inner bracket 46 are both formed of an elongated plate of rigid material such as steel. Outer plate 102 extends along its longest axis from top outer plate end 104 to bottom outer plate end 106, and inner plate 202 similarly extends along its longest axis from top inner plate end 204 to bottom inner plate end 206. Outer plate 102 and inner plate 202 both have fastener openings (108 and 208, respectively) situated at their top ends and sized to receive bracket fastener 48 (see FIG. 2). Bottom plate ends 106 and 206 are retained to frame 32 by insertion into slot 34, as discussed above. In the illustrated embodiment, outer and inner plates 102 and 202 also have stiffening flanges (116 and 216, respectively) extending along their longest edges to provide increased structural rigidity and durability. Inner and outer brackets 44 and 46 are mated pieces, with inner plate 202 of inner bracket 46 directly abutting outer plate 102 of outer bracket 44 and inner stiffening flanges 216 fitting within outer stiffening flanges 116, when hose bracket assembly 36 is assembled.

Outer and inner plates 102 and 202 both have central openings (110 and 210, respectively) sized and shaped to receive and retain hose couplings 42 of pump hose 24. In the case of outer bracket 44, outer central opening 110 is an elongated hole defined by outer opening perimeter 212. This hole includes mountings 114, which are semi-circular collars sized to mate with hose couplings 42. In particular, mountings 114 have radius slightly greater than a narrowest portion (i.e. neck) of hose couplings 42, so as to snugly engage hose couplings 42 at these narrowest portions (see FIG. 6, discussed below). Mountings 114 are too narrow to engage the larger portions of hose couplings 42 (see FIGS. 6 and 2). The portion of outer opening perimeter 112 extending between mountings 114 can be substantially uncontoured, and provides a wide enough outer central opening to permit the entirety of both hose couplings 42 to be inserted therethrough.

Figure 5A:
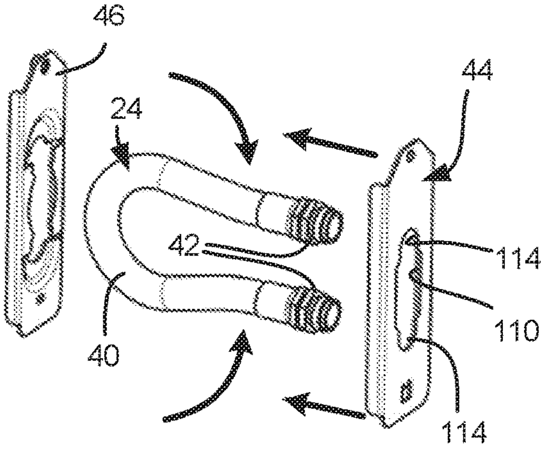
FIGS. 5A, 5B, and 5C are perspective views of the pump hose and hose bracket of FIG. 2 illustrating successive stages of installation of the pump hose.
Figure 5B:
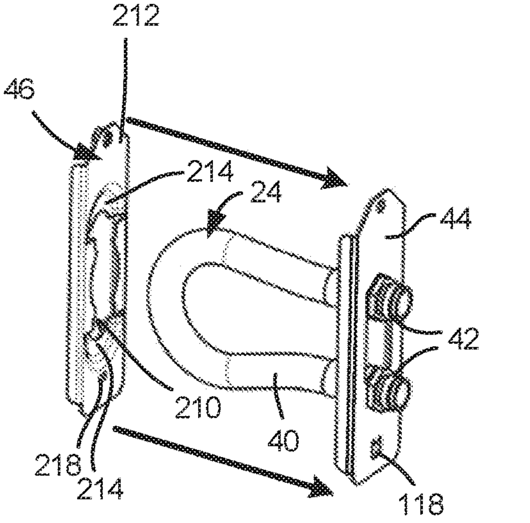
Figure 5C:
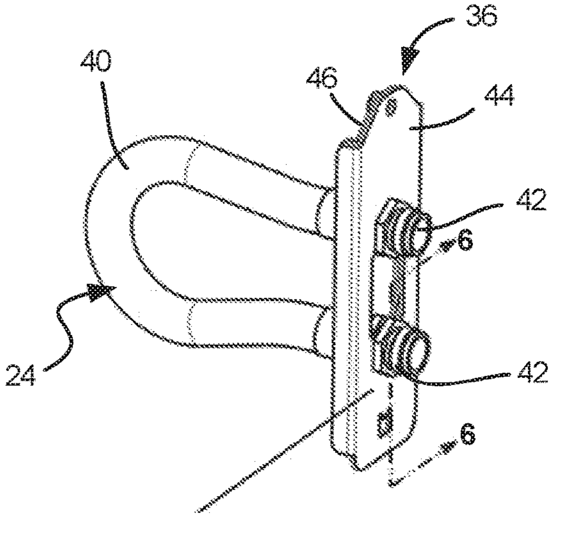

Inner bracket 46 fits over hose couplings 42 once hose couplings 42 are attached to mountings 114 (see FIGS. 5A-5C for details regarding the assembly of hose bracket assembly 36). Consequently, central opening 210 need not be sized large enough to for both hose couplings 42 to pass through, but is sized large enough for flexible section 40 of pump hose 24 to pass through. Central opening 210 is defined by central opening perimeter 212, which is shaped to permit inner plate 202 to abut inner faces of hose couplings 42, particularly at retainers 214. Retainers 214 are portions of inner plate 202 sized and shaped to contact hose couplings 42 while inner plate 202 abuts outer plate 102. In the illustrated embodiment retainers 214 are outwardly-bowled semicircular cups that align with mountings 114 when hose bracket assembly 36 is assembled.

The fit of inner bracket 46 and outer bracket 44 is facilitated by tab 118 and slot 218. Tab 118 is an outwardly-extending flange that fits through tab 218 when inner bracket 46 is engaged with outer bracket 44. Tab 118 and slot 218 serve as mistakeproofing function, preventing inner and outer brackets 46 and 44 from being assembled together at incorrect orientations. In addition, the engagement of tab 118 and slot 218 helps to hold hose bracket assembly 36 together while and until it is installed onto frame 32.

FIGS. 5A, 5B, and 5C are perspective views of pump hose 24, inner bracket 44, and outer bracket 46 in successive stages of installation of pump hose 24 onto bracket assembly 36. FIG. 5C additionally illustrates section plane 6-6, which defines the section of FIG. 6 (see below).

FIG. 5A illustrates a first installation step wherein opposite ends of pump hose 24 are brought together, bending flexible section 40 into a "U" or horseshoe shape. Hose couplings 42 are inserted through outer central opening 110 of outer bracket 44, and then released. Flexible section 40 has a degree of natural rigidity tending to bias it towards a substantially unbent shape. This natural bias retains hose couplings 42 against mountings 114 of outer central opening 110 even after pump hose 24 is released.

FIG. 5B illustrates a second installation step wherein inner bracket 46 is slid over flexible section 40 of pump hose 36 to directly abut hose couplings 42 at retainers 214, and outer bracket 44 along the rest of inner plate 202. In this position, inner bracket 46 prevents hose couplings 42 from disengaging from outer bracket 44, and tab 118 fits through slot 218. FIG. 5C depicts the resulting configuration of hose bracket assembly 36 and pump hose 24, and illustrates section plane 6-6.

Figure 6:
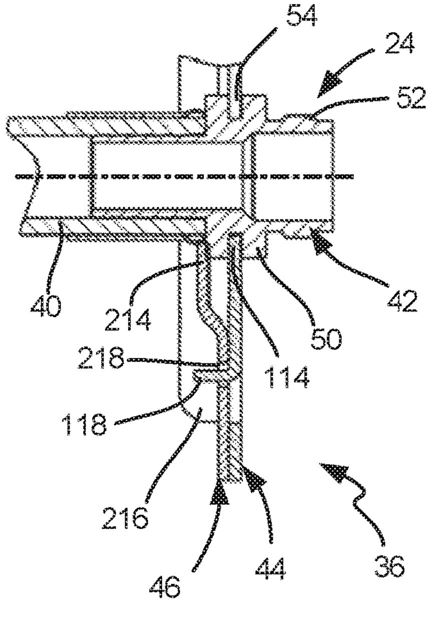
FIG. 6 is a cross-sectional view of the pump hose and hose bracket as installed in FIG. 5C.

FIG. 6 is a partial cross-sectional view of pump hose bracket assembly 36 and pump hose 24, illustrating the fit between pump hose 24, outer bracket 44, and inner bracket 46. FIG. 6 depicts brackets 44 and 46 substantially as discussed above, and further depicts coupling lug 50, coupling threading 52, and coupling neck 52 of hose coupling 42 of pump hose 24. Coupling lug 50 forms the thickest portion of hose coupling 42, and can for example be shaped in a polygonal fashion (e.g. hexagonal) to for easier manipulation. Coupling threading 52 is threading sized and shaped to mate with adjacent fluid handling components in a fluid seal. Coupling neck 54 is a narrowed annular groove in coupling lug 50, and is sized slightly smaller than mountings 114 to as to fit within mountings 114. Outer bracket 44 directly abuts inner bracket 46, and both brackets sandwich coupling lug 50 to reduce or eliminate vibration of hose coupling 42 with respect to hose bracket assembly 36. In addition, tab 118 fits through slot 218 when outer bracket 44 is assembled to inner bracket 46.

As discussed above, hose bracket assembly 36 provides an affordable and reliable means of quickly installing and removing pump hose 24 for easy replacement without additional tools. The design of hose bracket assembly 36 utilizes the natural bias of pump hose 24 towards a substantially open state to retain pump hose 24 against outer bracket 44 while fitting together hose bracket assembly 36.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

DISCUSSION OF POSSIBLE EMBODIMENTS

The following are non-exclusive descriptions of possible embodiments of the present invention.

A peristaltic pump having a drive assembly rotatable within a frame to move a plurality of rollers along a pumping path with respect to the frame, the peristaltic pump comprising: a pump hose having rigid hose ends connected by a bendable hose section with stiffness tending to bias the pump hose towards a substantially unbent shape; and an outer hose bracket having a rigid body with a first central opening sized to receive the rigid hose ends at first and second retention locations, such that bias of the pump hose towards a substantially unbent shape retains the hose ends within the first and second retention locations, positioning the bendable hose section along the pumping path of the rollers.

The peristaltic pump of the preceding paragraph can optionally include, additionally and/or alternatively, any one or more of the following features, configurations and/or additional components:

A further embodiment of the foregoing peristaltic pump, further comprising an attachment mechanism fastenable to secure the outer hose bracket to the frame, and unfastenable to permit the outer hose bracket to be withdrawn from the frame and drive assembly together with the pump hose.

A further embodiment of the foregoing peristaltic pump, wherein the rigid body of the outer hose bracket comprises a substantially flat plate, and wherein the attachment mechanism comprises a screw insertable through the substantially flat plate and into the frame.

A further embodiment of the foregoing peristaltic pump, wherein the screw is insertable through a first end of the substantially flat plate, and wherein a second end of the substantially flat plate substantially opposite the first end is insertable into a slot in the frame, such that tightening the screw locks the second end into the slot.

A further embodiment of the foregoing peristaltic pump, wherein the first and second retention locations comprise semi-circular mountings at opposite ends of the first central opening, each semi-circular mounting having a mounting radius sized to receive a rigid hose end.

A further embodiment of the foregoing peristaltic pump, wherein the each rigid hose end has a coupling lug too large to fit within the semi-circular mounting, and an annular slot forming a neck in the coupling lug with a radius slightly smaller than the edge radius, and therefore capable of engaging the semi-circular mounting.

A further embodiment of the foregoing peristaltic pump, further comprising an inner hose bracket securable to the outer hose bracket to lock the pump hose within the outer hose bracket by preventing the coupling lug from disengaging the semi-circular mountings.

A further embodiment of the foregoing peristaltic pump, wherein the inner hose bracket comprises a retention plate with a flat section that abuts the outer hose bracket when the inner hose bracket is secured to the outer hose bracket, and first and second collars where the retention plate bulges away from the outer hose bracket around the semi-circular mountings to accommodate the coupling lugs of the hose ends.

A further embodiment of the foregoing peristaltic pump, wherein the first and second collars are spaced away from the flat section by substantially the distance between an inner end of the each neck and the annular slot, such that the first and second collars retain the rigid hose ends tightly against the inner hose brackets when the inner hose bracket is secured to the outer hose bracket.

A further embodiment of the foregoing peristaltic pump, wherein the inner hose bracket defines a second central opening within the retention plate, the second central opening being large enough to accommodate the pump hose.

A further embodiment of the foregoing peristaltic pump, wherein the inner and outer hose brackets each have stiffening flanges.

A further embodiment of the foregoing peristaltic pump, wherein the outer hose bracket has an alignment tab, and the inner hose bracket has an alignment slot disposed to receive the alignment tab, such that securing the inner hose bracket to the outer hose bracket comprises inserting the alignment tab through the alignment slot.

A further embodiment of the foregoing peristaltic pump, wherein the alignment tab and alignment slot provide mistakeproofing by preventing the inner hose bracket from being secured to the outer hose bracket in any orientation other than a correct orientation.

A further embodiment of the foregoing peristaltic pump, wherein abutting first ends of the inner and outer hose brackets are together insertable into a shared retention slot in the frame, and abutting seconds ends of the inner and outer hose brackets opposite the first ends are securable to the frame via a fastener passing though the inner and outer hose brackets, such that the fastener locks the first ends of the inner and outer hose brackets into the shared retention slot when attached.

A texture sprayer comprising: the foregoing peristaltic pump; a motor disposed to drive the drive assembly of the peristaltic pump; a texture material source connected fluidly upstream of the peristaltic pump; a texture hose extending fluidly downstream from the peristaltic pump; and a spray gun situated at a downstream end of the texture hose, and actuatable to spray texture material pressurized by the peristaltic pump.

A further embodiment of the foregoing peristaltic pump, wherein the drive assembly is movable with respect to the pump hose, such that the rollers engage the pump hose only while the texture sprayer is in use.

An installation method for a pump hose of a peristaltic pump, the method comprising: bending a flexible section of the pump hose to bring together hose couplings of the pump hose at either end of the flexible section; inserting the hose couplings into a central opening of an outer hose bracket; releasing the pump hose, such that a natural unbending bias of the flexible section retains the hose couplings at mounting locations of the central opening; attaching an inner hose bracket to simultaneously abut the hose couplings and the outer hose bracket, thereby discouraging the pump hose from disengaging from the outer hose bracket; and locking the inner and outer hose brackets together into a location where the pump hose abuts rollers of the peristaltic pump.

The method of the preceding paragraph can optionally include, additionally and/or alternatively, any one or more of the following features, configurations and/or additional components:

A further embodiment of the foregoing method, wherein locking the inner and outer hose brackets together into a location where the pump hose abuts rollers of the peristaltic pump comprises inserting first ends of the inner and outer hose brackets into a retention slot of a rigid frame, and attaching a fastener through second ends of the inner and outer hose brackets opposite the first ends to lock both hose brackets into the retention slot.

A further embodiment of the foregoing method, wherein inserting the first ends of the hose brackets into the retention slot and attaching the fastener tightly secures the inner hose bracket against both the outer hose bracket and the hose couplings of the pump hose, thereby reducing or eliminating vibration of the pump hose with respect to the frame and the inner and outer hose brackets.

A further embodiment of the foregoing method, wherein the fastener is a threaded screw, such that attaching the fastener comprises inserting the fastener through the inner and outer hose brackets and threading the fastener into the frame.

SUMMATION

Any relative terms or terms of degree used herein, such as “substantially”, “essentially”, “generally”, “approximately” and the like, should be interpreted in accordance with and subject to any applicable definitions or limits expressly stated herein. In all instances, any relative terms or terms of degree used herein should be interpreted to broadly encompass any relevant disclosed embodiments as well as such ranges or variations as would be understood by a person of ordinary skill in the art in view of the entirety of the present disclosure, such as to encompass ordinary manufacturing tolerance variations, incidental alignment variations, alignment or shape variations induced by thermal, rotational or vibrational operational conditions, and the like.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A peristaltic pump having a drive assembly rotatable within a frame to move a plurality of rollers along a pumping path with respect to the frame, the peristaltic pump comprising:

a pump hose having rigid hose ends connected by a bendable hose section with stiffness tending to bias the pump hose towards a substantially unbent shape; and an outer hose bracket having a rigid body comprising a substantially flat plate with a first central opening circumscribed by a perimeter defining first and second outer openings extending outwardly at opposite ends of the first central opening and defining first and second retention locations such that the first and second retention locations are sized to receive the rigid hose ends, and such that bias of the pump hose towards a substantially unbent shape retains the hose ends within the first and second retention locations, positioning the bendable hose section along the pumping path of the rollers.

2. The peristaltic pump of claim 1, further comprising an attachment mechanism fastenable to secure the outer hose bracket to the frame, and unfastenable to permit the outer hose bracket to be withdrawn from the frame and drive assembly together with the pump hose.

3. The peristaltic pump of claim 2, wherein the attachment mechanism comprises a screw insertable through the substantially flat plate and into the frame.

4. The peristaltic pump of claim 3, wherein the screw is insertable through a first end of the substantially flat plate, and wherein a second end of the substantially flat plate substantially opposite the first end is insertable into a slot in the frame, such that tightening the screw locks the second end into the slot.

5. The peristaltic hose of claim 1, wherein the first and second retention locations comprise semi-circular mountings at opposite ends of the first central opening, each semi-circular mounting having a mounting radius sized to receive a rigid hose end.

6. The peristaltic hose of claim 5, wherein the each rigid hose end has a coupling lug too large to fit within the semi-circular mounting, and an annular slot forming a neck in the coupling lug with a radius slightly smaller than the edge radius, and therefore capable of engaging the semi-circular mounting.

7. The peristaltic pump of claim 6, further comprising an inner hose bracket securable to the outer hose bracket to lock the pump hose within the outer hose bracket by preventing the coupling lug from disengaging the semi-circular mountings.

8. The peristaltic pump of claim 7, wherein the inner hose bracket comprises a retention plate with a flat section that abuts the outer hose bracket when the inner hose bracket is secured to the outer hose bracket, and first and second collars where the retention plate bulges away from the outer hose bracket around the semi-circular mountings to accommodate the coupling lugs of the hose ends.

9. The peristaltic pump of claim 8, wherein the first and second collars are spaced away from the flat section by substantially the distance between an inner end of the each neck and the annular slot, such that the first and second collars retain the rigid hose ends tightly against the inner hose brackets when the inner hose bracket is secured to the outer hose bracket.

10. The peristaltic pump of claim 8, wherein the inner hose bracket defines a second central opening within the retention plate, the second central opening being large enough to accommodate the pump hose.

11. The peristaltic pump of claim 7, wherein the inner and outer hose brackets each have stiffening flanges.

12. The peristaltic pump of claim 7, wherein the outer hose bracket has an alignment tab, and the inner hose bracket has an alignment slot disposed to receive the alignment tab, such that securing the inner hose bracket to the outer hose bracket comprises inserting the alignment tab through the alignment slot.

13. The peristaltic pump of claim 12, wherein the alignment tab and alignment slot provide mistakeproofing by preventing the inner hose bracket from being secured to the outer hose bracket in any orientation other than a correct orientation.

14. The peristaltic pump of claim 7, wherein abutting first ends of the inner and outer hose brackets are together insertable into a shared retention slot in the frame, and abutting seconds ends of the inner and outer hose brackets opposite the first ends are securable to the frame via a fastener passing though the inner and outer hose brackets, such that the fastener locks the first ends of the inner and outer hose brackets into the shared retention slot when attached.

15. A texture sprayer comprising:

the peristaltic pump of claim 1, a motor disposed to drive the drive assembly of the peristaltic pump;

a texture material source connected fluidly upstream of the peristaltic pump;

a texture hose extending fluidly downstream from the peristaltic pump; and a spray gun situated at a downstream end of the texture hose, and actuatable to spray texture material pressurized by the peristaltic pump.

16. The texture sprayer of claim 15, wherein the drive assembly is movable with respect to the pump hose, such that the rollers engage the pump hose only while the texture sprayer is in use.

17. A peristaltic pump having a drive assembly rotatable within a frame to move a plurality of rollers along a pumping path with respect to the frame, the peristaltic pump comprising:

a pump hose having rigid hose ends connected by a bendable hose section with stiffness tending to bias the pump hose towards a substantially unbent shape;

an outer hose bracket having a rigid body with a first central opening sized to receive the rigid hose ends at first and second retention locations, such that bias of the pump hose towards a substantially unbent shape retains the hose ends within the first and second retention locations, positioning the bendable hose section along the pumping path of the rollers; and a retention slot in the frame, wherein the outer hose bracket is insertable into the retention slot to retain the outer hose bracket in the frame.

18. A peristaltic pump having a drive assembly rotatable within a frame to move a plurality of rollers along a pumping path with respect to the frame, the peristaltic pump comprising:

a pump hose having a pair of rigid metal hose ends connected by a middle bendable hose section between the pair rigid metal hose ends, the middle bendable hose section having stiffness tending to bias the pump hose towards a substantially unbent shape; and an outer hose bracket having a rigid body with a first central opening circumscribed by a perimeter defining first and second outer openings extending outwardly at opposite ends of the first central opening and defining first and second retention locations such that the first and second retention locations are sized to receive the pair of rigid metal hose ends, and such that both of the pair of rigid metal hose ends contact the outer hose bracket at the first and the second retention locations and both of the pair of rigid metal hose ends extend through the first central opening, wherein bias of the pump hose towards a substantially unbent shape retains the rigid metal hose ends within the first and second retention locations and the middle bendable hose section extends away from the outer hose bracket when the pump hose is mounted on the outer hose bracket, the receiving of the pair of rigid metal hose ends at the first and the second retention locations of the outer hose bracket positioning the bendable hose section along the pumping path of the rollers.

19. The peristaltic pump of claim 18, further comprising an inner hose bracket securable to the outer hose bracket to lock the pump hose within the outer hose bracket by preventing the metal fittings from disengaging from the first and second retention locations.

20. The peristaltic pump of claim 18, further comprising an attachment mechanism operable to fasten the outer hose bracket to the frame, and to unfasten the outer hose bracket from the frame to permit the outer hose bracket to be withdrawn from the frame together with the pump hose.

* * * * *